(12) United States Patent
Stauffer

(10) Patent No.: US 7,276,635 B2
(45) Date of Patent: Oct. 2, 2007

(54) METHYL HALIDE PROCESS

(76) Inventor: John E. Stauffer, 6 Pecksland Rd., Greenwich, CT (US) 06830

( * ) Notice: Subject to any disclaimer, the term of this patent is extended or adjusted under 35 U.S.C. 154(b) by 305 days.

(21) Appl. No.: 10/938,687

(22) Filed: Sep. 10, 2004

(65) Prior Publication Data

US 2006/0058559 A1    Mar. 16, 2006

(51) Int. Cl.
*C07C 17/00* (2006.01)
(52) U.S. Cl. .................................................. 570/240
(58) Field of Classification Search ................. 570/240
See application file for complete search history.

(56) References Cited

U.S. PATENT DOCUMENTS

| 4,041,087 A | 8/1977 | Vannice |
| 4,538,011 A | 8/1985 | Drago et al. |
| 4,845,064 A | 7/1989 | Drago et al. |
| 4,962,247 A | 10/1990 | Holbrook et al. |

OTHER PUBLICATIONS

Kirk-Othmer, Encyclopedia of Chemical Technology, pp. 101-102, 1034, vol. 5, 4th edition, publ. John Wiley & Sons, Oct. 2003.
Kirk-Othmer, Encyclopedia of Chemical Technology, pp. 905-906, vol. 13, 4th edition, publ. John Wiley & Sons, Oct. 2003.
Kirk-Othmer, Encyclopedia of Chemical Technology, pp. 539-541, vol. 16, 4th edition, publ. John Wiley & Sons, Oct. 2003.
Kirk-Othmer, Encyclopedia of Chemical Technology, p. 368, vol. 19, 4th edition, publ. John Wiley & Sons, Oct. 2003.

*Primary Examiner*—Johann Richter
*Assistant Examiner*—Yevgeny Valenrod
(74) *Attorney, Agent, or Firm*—YoungBasile PC

(57) ABSTRACT

A process is provided for the production of a methyl halide by reacting carbon monoxide, hydrogen, and hydrogen halide over a catalyst to give methyl halide and carbon dioxide. The reaction is carried out under anhydrous conditions by using a ratio of carbon monoxide to hydrogen of 2-2.5:1. The catalyst contains a metal from the group copper and zinc. High conversion and yields are obtained in the process.

1 Claim, 2 Drawing Sheets

METHYL HALIDE PROCESS

FIELD OF THE INVENTION

The present invention relates to a process for the manufacture of methyl halides including methyl chloride, methyl bromide, and methyl iodide. In the process, carbon monoxide, hydrogen and a hydrogen halide are reacted in the presence of a catalyst to produce a methyl halide and carbon dioxide. The carbon monoxide and hydrogen may be supplied from synthesis gas.

BACKGROUND OF THE INVENTION

Traditionally the two principal methods of producing methyl chloride have been the chlorination of methane and the hydrochlorination of methanol. Each of these processes has certain disadvantages. The chlorination of methane produces hydrogen chloride as a byproduct, and it generates higher chlorinated methane products such as methylene chloride and chloroform. The hydrochlorination of methanol is dependent on the raw material methanol which adds to the cost of process.

Because of the limitations of current technology, several attempts have been made to synthesize methyl chloride from carbon monoxide, hydrogen, and hydrogen chloride. Such a process would have the benefit of using synthesis gas as a raw material and could utilize byproduct hydrogen chloride from other processes. Four U.S. patents disclose such processes to make methyl chloride: U.S. Pat. Nos. 4,041,087, 4,538,011, 4,845,064, and 4,962,247.

Although the results of these investigations are encouraging, in each case they suffer from serious drawbacks. Uniformly their conversions are limited. In addition, the yields of methyl chloride are reduced due to the production of byproducts. Furthermore, processing conditions are highly corrosive. Finally, the use of precious metals in the catalysts adds to the manufacturing costs.

An object of the present invention is to avoid the disadvantages of the prior art by providing a superior process for the manufacture of methyl halide from carbon monoxide, hydrogen, and hydrogen halide. A further object is to achieve high conversions and maximum yields. A still further object of the present invention to provide a process that is efficient, reliable, safe, and environmentally friendly. These and other objects, features and advantages will be apparent from the following description.

SUMMARY OF THE INVENTION

In one particular embodiment of the present invention, carbon monoxide, hydrogen and a hydrogen halide are reacted over a catalyst in a reactor to give a methyl halide and carbon dioxide according to the following equation:

$$2CO + H_2 + HX \rightarrow CH_3X + CO_2 \qquad 1.$$

where X represents a halogen, including chlorine, bromine and iodine.

According to the stoichiometry of the reaction, two moles of carbon monoxide react with one mole of hydrogen. There is an advantage, however, in using an excess of carbon monoxide so that the invention contemplates the use of a ratio of carbon monoxide to hydrogen in the feed stream to the reactor in the range of 2-2.5:1.

The catalyst for the process comprises a metal from the group copper and zinc. The catalyst may be a mixture of particles or pellets with distinct compositions. These compositions include zinc-chromium oxide, copper-zinc-alumina, cuprous chloride on active alumina, zinc chloride on active alumina, and zinc oxide-copper oxide.

The operating conditions are determined by the equilibrium of the reaction and its kinetics. The preferred temperature is in the range of about 200° to 400° C. The operating pressure is in the range of about one atmosphere to approximately 100 atmospheres. The process may function outside these limits but at some disadvantage.

DETAILED DESCRIPTION OF THE PROCESS

As applied to the production of methyl chloride, the present invention covers the reaction of carbon monoxide (CO), hydrogen ($H_2$), and hydrogen chloride (HCl) to give methyl chloride ($CH_3Cl$) and carbon dioxide ($CO_2$). A catalyst is required to promote this reaction, which can be represented by the following equation:

$$2CO + H_2 + HCl \rightarrow CH_3Cl + CO_2 \qquad 2.$$

This is the same reaction as that shown by more generalized equation no. 1.

The above reaction of equation no. 2 is the only one of several possible reactions that might be considered to produce methyl chloride from synthesis gas. For example, one mole of carbon monoxide can react with two moles of hydrogen and one mole of hydrogen chloride to give methyl chloride and water. Alternatively, one mole of carbon dioxide can react with three moles of hydrogen and one mole of hydrogen chloride to give methyl chloride and water.

Figure 1:
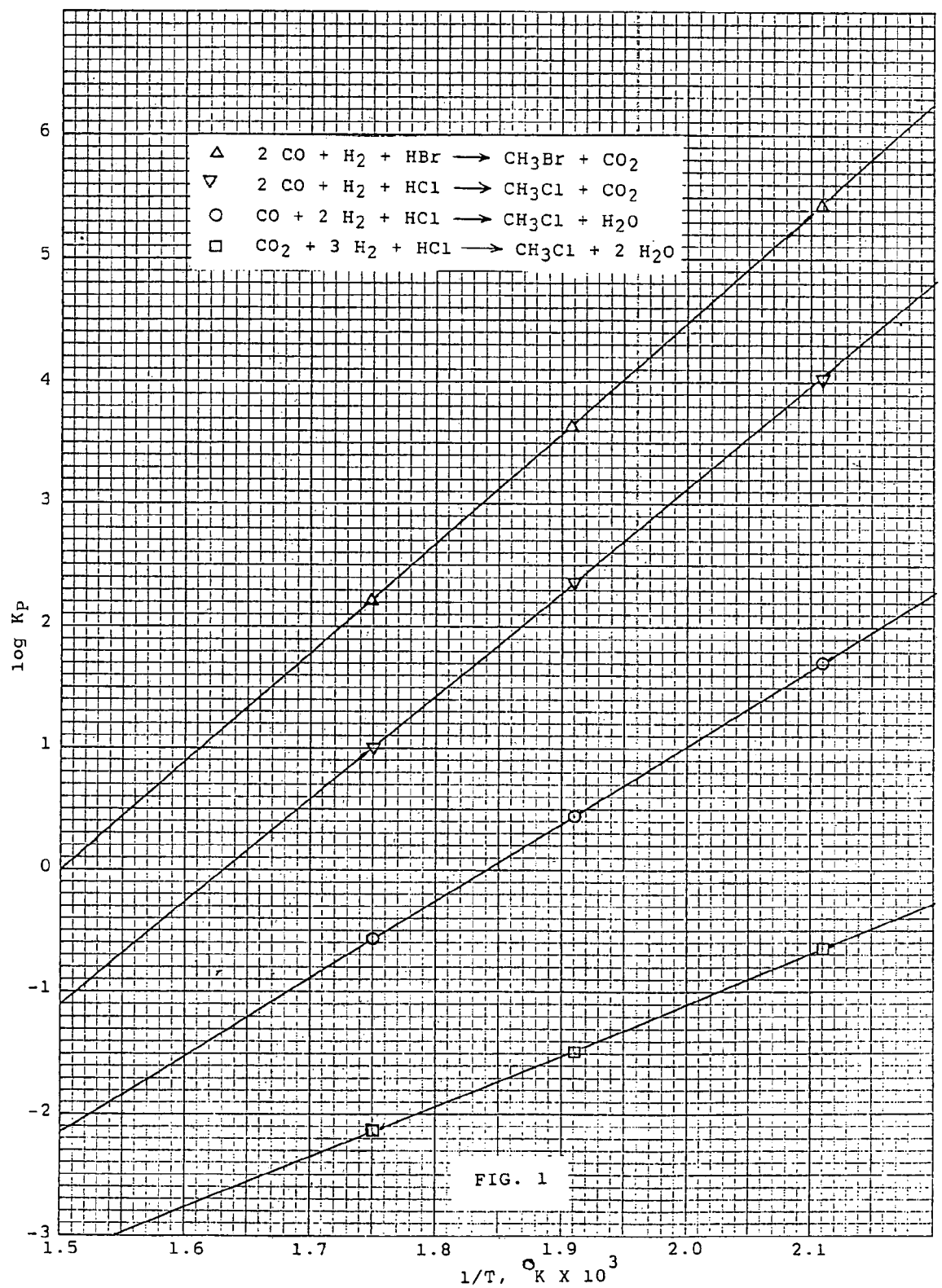
FIG. 1 is a plot of an equilibrium constant, shown logarithmically, against the reciprocal of temperature.

Which one of these possible reactions is selected is determined by equilibrium considerations. The reaction which provides the greatest conversion of reactants to product is the preferred one. Using thermodynamic data, the conversions for each of these reactions were determined at different temperatures, and the results are shown in FIG. 1 as the equilibrium constant $K_p$ plotted against the reciprocal of the absolute temperature, T. Included in this figure is the reaction for the formation of methyl bromide which is even more favorable than the reactions to produce methyl chloride.

All of the data shown in FIG. 1 indicate that conversions are incomplete within the ranges of temperature required by reaction kinetics. Fortunately, conversions can be increased by the application of pressure. According to the principle of Le Chatelier, elevated pressure will increase conversions because, as shown in equation no. 1, the volume of product gases is only one half the volume of reactant gases.

As already noted, the reaction of the present invention requires a catalyst. The type of catalyst can be determined from the mechanism of the reaction. The formation of methyl chloride from carbon monoxide, hydrogen, and hydrogen chloride can be considered the result of three separate reactions occurring in series. First, carbon monoxide and hydrogen react together to form methanol ($CH_3OH$). Second, the methanol from the first reaction combines with hydrogen chloride to give methyl chloride and water ($H_2O$).

Third, the water from the second reaction reacts with more carbon monoxide to produce carbon dioxide and hydrogen.

The three steps involved with the production of methyl chloride can be expressed by the following equations:

$$CO + 2H_2 \rightarrow CH_3OH \qquad 3.$$

$$CH_3OH + HCl \rightarrow CH_3Cl + H_2O \qquad 4.$$

$$H_2O + CO \rightarrow CO_2 + H_2 \qquad 5.$$

When equation nos. 3, 4, and 5 are combined, the result is the expression shown in equation no. 2.

Each of the reactions shown by equation nos. 3 through 5 requires a catalyst. These catalysts are well known and are reported in the literature. The reaction of equation no. 3 is catalyzed by a zinc-chromium oxide catalyst or by the more active copper-zinc-alumina catalyst. (Kirk-Other, *Encyclopedia of Chemical Technology*, 4$^{th}$ ed., John Wiley & Sons, Vol. 16 p. 539-541). The reaction may also be catalyzed by palladium. (ibid, Vol. 9, p. 368) The reaction of equation no. 4 known as methanol hydrochlorination is catalyzed by alumina gel, or cuprous chloride or zinc chloride on active alumina, carbon, silica, or pumice among other catalysts. (ibid, Vol. 5, p. 1034) Finally, the reaction of equation no. 5 is catalyzed by a reduced iron catalyst or the more active zinc oxide-copper oxide catalyst. (ibid, Vol. 5, pp. 101-102)

By coincidence, the catalysts for each of the reactions of equation nos. 3-5, with a few exceptions, all comprise either copper or zinc. These metals may be supported on a carrier such as active alumina. Furthermore, the catalysts which contain copper or zinc are the more active ones. Therefore, the catalyst of choice in the present invention comprises a metal from the group copper and zinc.

The formation of methyl chloride from carbon monoxide, hydrogen, and hydrogen chloride can be explained by an alternative mechanism. Again, three steps are involved. The first two reactors are identical to those given above by equation nos. 3 and 4. The third reaction involves the formation of carbon dioxide and hydrogen from methanol and water. This alternative mechanism can be represented by the following set of equations.

$$2CO + 4H_2 \rightarrow 2CH_3OH \qquad 6.$$

$$CH_3OH + HCl \rightarrow CH_3Cl + H_2O \qquad 4.$$

$$CH_3OH + H_2O \rightarrow CO_2 + 3H_2 \qquad 7.$$

When equation Nos. 6, 4, and 7 are added together, the result is identical to equation No. 2.

It should be noted that equation no. 7 represents the reversal of the reaction in which carbon dioxide and hydrogen combine to form methanol and water. As a result, it is catalyzed by the same catalyst used to produce methanol. According to this alternative mechanism, only two separate catalyst compositions are required: one for methanol synthesis and the other for methanol hydrochlorination.

The present invention contemplates the use of a catalyst mixture that contains two or three distinct compositions. The rational for this approach as opposed to the use of a single catalyst composition is that greater catalyst activity and selectivity can thereby be achieved. It is easier to develop a catalyst for a reaction involving two reactants than for a reaction where there are three reactants.

A distinguishing feature of the present invention is that the process is carried out under anhydrous conditions. This requirement greatly reduces potential corrosion. Not only is this feature an advantage in selecting materials of construction, but it promises to extend the catalyst life. Anhydrous hydrogen chloride is much less reactive with metals at all but elevated temperatures. (ibid, Vol. 13, p. 905-906)

In order to maintain anhydrous conditions in the process, an excess of carbon monoxide can be used in the feed to the reactor. This effect is shown by equation no. 5 where carbon monoxide scavenges water to produce carbon dioxide and hydrogen. The exact amount of carbon monoxide required is questionable, but a 25% excess would appear to be more than sufficient.

Operating conditions for the process are dictated by reaction kinetics. The more active catalyst for the reaction of equation No. 3 is effective in the range of 210° to 270° C. The less active catalyst requires a temperature between 320° and 450° C. The reaction of equation no. 4 needs a temperature anywhere from 295° to 350° C. And finally, for the reaction of equation No. 5, a temperature of 315° C. or lower is adequate, depending on the catalyst used. Putting all this information together suggests an operating temperature between 200° and 400° C.

As noted previously, higher operating pressures increase the conversion of the reaction. This effect greatly enhances the efficiency of the process. On the other hand, higher pressures require greater capital investment in equipment. The present invention has the advantage over the prior art of operating at lower pressures. This condition is an added safety feature.

The reaction shown by equation No. 1 is highly exothermic. Therefore heat must be removed from the reaction in order to control the temperature. This goal is achieved by proper reactor design. Either a fluidized bed reactor or a shell and tube reactor are helpful in this respect.

Figure 2:
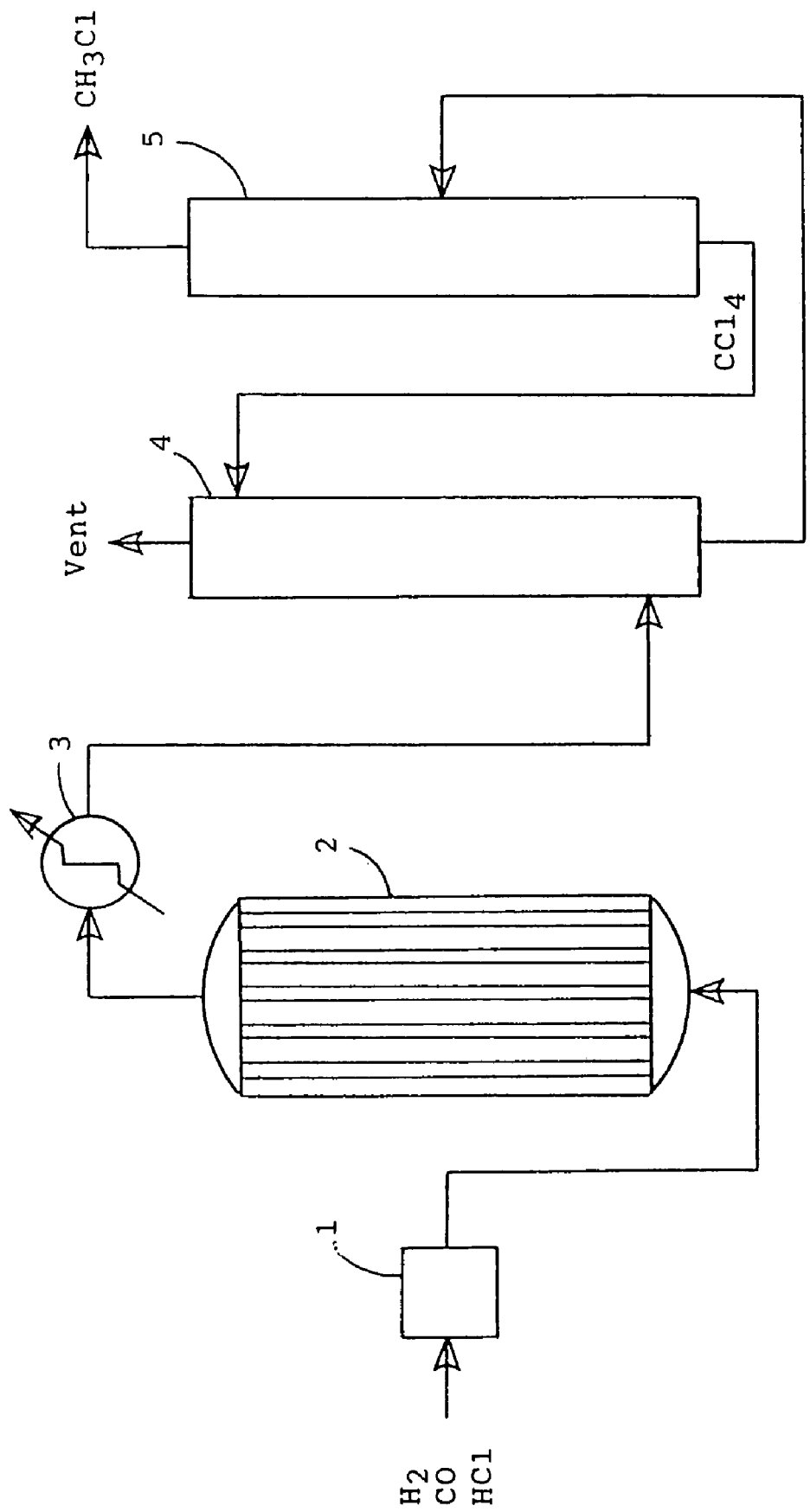
FIG. 2 is a diagram of an apparatus, for carrying out the invention.

A schematic flow sheet of the process is shown in FIG. 2. The reactants are heated in preheater 1 before being fed to reactor 2. The exit gases from the reactor are cooled in heat exchanger 3 before passing to extraction column 4 where a stream of carbon tetrachloride removes methyl halide from the gas stream. The methyl halide-laden carbon tetrachloride is fractionated in distillation column 5 to produce methyl halide product and regenerate the carbon tetrachloride solvent.

The vent gases from the process are scrubbed (not shown) to remove hydrogen halide, which is recycled to the reactor. This step increases the efficiency of the process and avoids an environmental hazard.

Methyl halide produced by the process is a valuable item of commerce. Methyl chloride is used to manufacture silicones and chlorinated solvents. Methyl bromide is widely used as a fumigant in agriculture. As the cost of methyl halide is reduced, new applications should develop.

EXAMPLES

1. Engineering calculations were made to determine the conversion of carbon monoxide, hydrogen and hydrogen chloride to methyl chloride and carbon dioxide at 300° C. and 10 atmospheres pressure. Using the data from FIG. 1, the logarithm of the equilibrium constant was determined to be +0.97. This is equivalent to 9.33 for $K_p$. The conversion was calculated to be 82.2%.

2. The same reaction as considered in example 1 was carried out but at a pressure of 100 atmospheres. Under this condition, the conversion equaled 94.3%.

3. In this example, the conversion of carbon monoxide, hydrogen, and hydrogen bromide to methyl bromide and carbon dioxide was considered. The conditions were 300° C.

and 100 atmospheres. Again, using the data from FIG. 1, the conversion was determined to be 97.2%.

What is claimed is:

1. A process for the production of a methyl halide in which the reaction between carbon monoxide, hydrogen, and a hydrogen halide to form a methyl halide and carbon dioxide is carried out over a catalyst, the ratio of carbon monoxide to hydrogen in the reactants being in the range of 2-2.5:1, said catalyst being selected from the group consisting of zinc-chromium oxide, copper-zinc-alumina, cuprous chloride, zinc chloride, and zinc oxide-copper oxide, and said reaction being conducted at a temperature in the range of 200° C. to 400° C. and at a pressure in the range of 1 atmosphere to 100 atmospheres.

* * * * *